United States Patent
Hohl

(10) Patent No.: US 8,551,165 B2
(45) Date of Patent: Oct. 8, 2013

(54) CASSETTE FOR INTRAOCULAR LENS AND PRELOADED LENS INJECTION SYSTEM

(75) Inventor: Emil Hohl, Au (CH)

(73) Assignee: Medicel AG (CH)

( * ) Notice: Subject to any disclaimer, the term of this patent is extended or adjusted under 35 U.S.C. 154(b) by 80 days.

(21) Appl. No.: 13/120,373

(22) PCT Filed: Sep. 18, 2009

(86) PCT No.: PCT/CH2009/000305
§ 371 (c)(1),
(2), (4) Date: Mar. 22, 2011

(87) PCT Pub. No.: WO2010/031196
PCT Pub. Date: Mar. 25, 2010

(65) Prior Publication Data
US 2011/0190777 A1    Aug. 4, 2011

(30) Foreign Application Priority Data
Sep. 22, 2008  (CH) ........................................ 1492/08

(51) Int. Cl.
*A61F 2/16*  (2006.01)
(52) U.S. Cl.
USPC ........................................................ 623/6.12
(58) Field of Classification Search
USPC ........................ 606/107; 623/4.1, 6.11, 6.12
See application file for complete search history.

(56) References Cited

U.S. PATENT DOCUMENTS

| 4,681,102 A | 7/1987 | Bartell |
| 5,582,614 A | 12/1996 | Feingold |
| 5,947,975 A | 9/1999 | Kikuchi et al. |
| 2002/0077633 A1 | 6/2002 | Kikuchi |
| 2004/0199174 A1 | 10/2004 | Herberger et al. |
| 2005/0049605 A1 | 3/2005 | Vaquero et al. |
| 2005/0125000 A1* | 6/2005 | Tourrette et al. ............. 606/107 |
| 2006/0235429 A1* | 10/2006 | Lee et al. ..................... 606/107 |
| 2007/0060925 A1 | 3/2007 | Pynson |

FOREIGN PATENT DOCUMENTS

| WO | WO 03/049645 | 6/2003 |
| WO | WO 2008/098384 | 8/2008 |

* cited by examiner

*Primary Examiner* — Ryan Severson
(74) *Attorney, Agent, or Firm* — Morris O'Bryant Compagni, PC

(57) ABSTRACT

A cassette (11) consists of a cassette body (13) with a space (19) for receiving an intraocular lens (IOL) (12) and a lid (23) for closing the cassette body. The cassette body (13) has openings (17a, 17b) on opposing side walls, wherein an injector piston (20) can penetrate through the opening (17b) and displace an IOL (12), which is received in the receiving space (19), out of the receiving space through the opening (17a). The cassette lid (23) seals the cassette body (13) hermetically from the environment. Coupling means, which allow the cassette body (13), which is closed by the lid, to be fastened to an injector (31), are provided on the cassette body (13). The cassette (11) can be inserted into the aperture (39) of an injector (31) in the closed state. For injecting the lens (12), which is received in the receiving space (19), the cassette (11) can be made to pivot into an injection position.

10 Claims, 5 Drawing Sheets

CASSETTE FOR INTRAOCULAR LENS AND PRELOADED LENS INJECTION SYSTEM

CROSS-REFERENCE TO RELATED APPLICATIONS

This application claims priority to PCT patent application No. PCT/CH2009/000305 filed on Sept. 18, 2009 and Swiss Patent Application No. 1492/08 filed on Sept. 22, 2008, the entirety of each of which is incorporated by this reference.

BACKGROUND OF THE INVENTION

1. Field of the Invention

The invention relates to a cassette for an intraocular lens and also to an injection system for ejecting an intraocular lens from the cassette.

2. State of the Art

Nowadays, in cataract operations, an artificial lens, what is known as an intraocular lens (IOL), is implanted as standard into the capsular bag of the eye. During the operation, an ocular incision of from typically 2 to 4 mm is formed through which the natural eye lens is removed and replaced by the implant. In order to remove the natural eye lens, the natural eye lens is first destroyed by means of ultrasound and then extracted by suction. After removal of the natural eye lens, the artificial lens is introduced, in the folded state, through the incision into the capsular bag. As soon as the folded lens has been introduced into the capsular bag, the lens unfolds again into its original shape.

Improved operation tools and implants allow the surgeon to make the incisions smaller than in the past. Nowadays, the natural eye lens can be removed even through an incision of about 2 mm. However, this only makes sense if the intraocular lens can also be inserted through the same incision.

Cartridges, into which a lens can be loaded and then ejected out of the cartridge by means of an injector, have been developed in recent years for inserting an intraocular lens. Examples of cartridges and injectors of this type are known from American patents U.S. Pat. Nos. 4,681,102, 5,582,614, 5,947,975 and US patent application No. 2004/0199174.

In the injector device according to U.S. Pat. No. 4,681,102, the cartridge, which is embodied as a device for folding the lens, and the injector nozzle are separate parts. The cartridge can be inserted into the injector housing, whereupon the injector nozzle can be screwed at the front onto the injector housing.

In the injector device according to U.S. Pat. No. 5,582,614 and most previously known injector devices, the cartridge consists in one piece of a folding device and an injector nozzle.

US 2004/0199174 shows in FIG. 2 an injector device in which the injector housing consists in one piece of a cylinder for receiving the piston, a device for folding the lens and an injector nozzle.

The most commonly used intraocular lenses are made from a hydrophilic material. Lenses of this type are delivered in a liquid bath, packaged in a sterile manner by the manufacturer. Storage in a liquid is necessary to prevent the lens from drying out. During the operation, the lens has to be removed from the packaging and inserted into the cartridge, whereupon this cartridge can then be loaded into the injector. As these are very small and resilient structures, there is a certain risk, during fitting of the cartridge, that the lens will fall out or jump away during folding and thus lose its sterny. This risk is particularly great in cartridges according to U.S. Pat. No. 4,681,102 which provides no measures for grasping the edges of the lens during folding.

US 2005/0049605 discloses an already loaded injection device with an injector body and an injector nozzle adjoining the injector body. The injector nozzle has, adjacent to the injector body, an aperture which serves to receive an IOL. The IOL is, in the unstressed state, held in the aperture by a mount which can be inserted from above. Mutually set-apart guide elements are molded laterally onto the aperture on one side of the aperture. The guide elements serve to receive a movable compression load which is displaceable perpendicularly to the longitudinal extension of the injection device. The compression load can be used to compress the IOL, once the mount has been removed, and to bring it into a state which is ready for injection. The injection device of US 2005/0049605 is already loaded by the manufacturer with an IOL and dispatched in a sterilized packaging. The advantage of the injection device of US 2005/0049605 is that the IOL is already inserted into the injection device and no longer has to be directly grasped by the surgeon. Nevertheless, a drawback of the injection device is that the device is suitable only for hydrophobic lenses, as the lens cannot be stored in liquid.

US 2007/0060925 discloses a system which also allows the preloading of hydrophilic lenses.

In this case, the system is divided into a distal and a proximal part. The distal part contains in this case the lens (IOL), the lens container and the cartridge and is sterilized and stored together in an additional, hermetically sealed container filled with liquid. Once the container has been opened, the distal and proximal parts have to be assembled by the operating staff.

Although mention is also made of the possibility of being able to sterilize the distal and proximal parts also in assembled form in a container (vial), this would require a very large container and a large amount of liquid. Drawbacks of this proposed solution include the fact that the liquid runs out when the container is opened. A system of this type would, on account of its size, also be awkward and not particularly customer-friendly.

A cassette and an injector for flexible intraocular lenses (IOLs) have become known through WO 03/049645. The cassette consists of a base part and a lid which is articulated to the base part. A hollow space, which serves to receive the lens, is formed in the lid and in the base part. An inlet opening and an outlet opening are provided at mutually opposing sides of the cassette. A plunger can be introduced into the cassette through the inlet opening in order to eject the lens through the outlet opening. Projections, which serve to interact with corresponding parts on the injector in order to precisely position the cassette in the injector, are provided on the base part and on the Hd. The cassette of WO 03/049645 is also suitable for receiving hydrophilic lenses. In this case, the cassette, with the lens received therein, is placed into a hermetically sealable container, which is filled with liquid, and sterilized in the container. Once the container has been opened by the operating staff, the cassette is inserted into the injector. Alternatively, it is proposed to mount the cassette already onto the injector and to hermetically seal the entire injector in the container which is filled with liquid. However, this again requires large containers; this is not user-friendly.

US 2002/0077633 discloses an implantation system for a deformable intraocular lens with an injector and a cassette. The cassette consists of a cassette lower part and a cassette upper part which, joined together, define space for receiving a lens. The cassette has at mutually opposing sides openings through which a piston of an injector can penetrate. A projection, which fits into a recess on the injector, is at the bottom of the cassette lower part. If the cassette is loaded into the injector, then the cassette is precisely positioned and the openings are coaxial with the displaceable piston.

All the cassettes described hereinbefore have in common the fact that the openings are not closed for the passing of the injector piston and the issuing of the lens. The storage of lenses which have to be stored in liquid therefore necessitates in all cases a further container which is filled with liquid and in which the cassette can be stored in a hermetically sealed manner.

As described hereinbefore, cassettes in which hydrophilic IOLs are already preloaded are commercially available. The injector has, before the injector nozzle, an insertion receptacle into which the cassette is inserted. The cassette is removed from its container (wet packaging) with storage liquid and inserted into the injector. In order to prevent the IOL from slipping during the transfer in the cassette, the cassette is equipped with an interlocking device. As soon as the cassette is in the insertion device of the injector, the interlocking is broken off and the IOL is released for injection into the eye. The fact that the IOL is transferred to the injector in a cassette protecting the IOL is advantageous. Nevertheless, the drawback of the cassette is that it is very small and accordingly difficult to grasp using two fingers. A further drawback is that the IOL has direct contact with the environment, in the time from the removal of the packaging up to the fixing in the injector, via openings in the cassette which serve to introduce the injector piston and eject the IOL. Thus, accidental dropping of the cassette can render the IOL unusable.

It is therefore an advantage of the present invention to propose a cassette and an injector system comprising a cassette and injector that minimize the number of required manual interventions which are necessary during the surgical use of the IOL. A further advantage is to disclose means and ways as to how the lens, which is in particular stored in liquid, can be loaded into the device as early as during manufacture and remains securely positioned, after loading up to the operation, without the cassette, or even the entire injector, having in this case to be stored in an additional wet container.

SUMMARY OF THE INVENTION

According to the invention, in a cassette of the type mentioned at the outset, this is achieved in that, when the cassette is closed, the cassette lid closes the receiving space and the openings. The cassette according to the invention has the advantage over the previously used cassettes that a hydrophilic lens can be sterilized directly in the cassette and stored for a relatively long time, as the cassette lid hermetically seals the receiving space from the environment. The cassette can then be inserted, prior to sterilization, into an injection device and be jointly sterilized with the injection device and is then ready for use. Alternatively, the cassette can also be sterilized separately from the injection device and be inserted into the injection device only prior to the implantation of the lens. Both procedures have the advantage that the surgeon does not need to grasp the lens or have to carry out other manual loading actions. The lens may be sterilized already in the cassette. For this purpose, the cassette may be made from a biocompatible plastics material which is suitable for the sterilization of the IOL-required temperatures of over 120° C.

A seal is provided between the edge of the cassette lid and the cassette body. The seal ensures reliable sealing of the receiving space from the environment. In principle, the cassette lid and cassette body can have different forms. However, it is important that the lid is able to seal the openings of the cassette body. In principle, the lid can be designed in one, two or a plurality of pieces. Advantageously, the cassette body is at least partially received in the cassette lid in a form-fitting manner. Expediently, the seal is arranged in a peripheral groove at the housing circumference of the cassette body.

Advantageously, a first coupling means of the cassette rotatably interacts with a second coupling means on the injector. These coupling means can be configured differently. In one embodiment, the first coupling means can be formed by a journal and the second coupling means can be formed by a journal receptacle or vice versa. According to an advantageous embodiment, mutually interacting locking means, for example in the form of projections or undercuts and locking points interacting therewith, are also provided on the cassette and the injector. The locking means prevent the cassette and injector from being able to be separated from each other without destruction once the cassette has been inserted into the injector. Advantageously, the cassette body has at the outside a peripheral sealing edge against which the cassette lid can rest, in the closed state of the cassette, so as to produce a seal.

Expediently, interlocking means are provided on the cassette lid and cassette body in order to releasably join together the cassette lid and cassette body. These interlocking means are designed as pivot levers which can interact with the cassette body at mutually opposing sides. The pivot levers are in this case rotatably arranged on two molded-on extensions at the narrow sides of the cassette lid. In the interlocking position of the pivot levers, the cassette lid is pressed against the cassette body. The interacting of the lid wall and sealing edge reliably seals the cassette body from excess pressures which are inevitably produced during sterilization processes. It is conceivable to form, instead of the above-described interlocking system, a snap connection between the cassette lid and the cassette body. This snap connection can be formed by undercuts and locking points provided on the lid and the cassette body.

The subject of the present invention is also an injector system, which comprises a cassette arranged in or that can be arranged in the aperture. The injector system according to the invention has the advantage that the system can be dispatched in a completely sterile manner and the cassette body can be integrated into the injector system already in the dispatch state. As a result, the IOL no longer has to be loaded into the injector before the operation.

The above-described cassette is expediently arranged in an aperture provided between the injector nozzle and injector body, the distance between the injector nozzle and the injector body being designed in such a way that the cassette body can be rotated in the aperture by at least 90°. Alternatively, the closed cassette can also be arranged on the injection device in such a way that the openings are already oriented axially in the longitudinal direction of the injection device. This has the advantage that the cassette no longer has to be rotated prior to the injecting of the IOL. However, in this case, there would be a small gap between the cassette body and the injection nozzle once the cassette lid has been detached. This gap may be overcome if the injection nozzle and/or cassette body are arranged on a support so as to be axially movable relative to each other, so that the injection nozzle and cassette body can be pushed together prior to the injecting and once the cassette lid has been removed. The cassette and/or nozzle can be fixed relative to each other by providing suitable arresting or locking means on the cassette body and support.

Advantageously, the injector body and the injector nozzle are molded onto a support. This support has the advantage that stable fastening of the cassette to the support is ensured and the openings of the cassette body are arranged, during the injection, coaxially with the injector piston.

Expediently, coupling means are provided on the cassette body and on the support in order to connect the cassette body to the injector and to orient it. In another embodiment, a journal is embodied on the cassette body and a cylindrical journal receptacle is embodied on the support. The journal and journal receptacle have the advantage that the cassette body may be rotated on a guided circular path. A clip fixes the cassette body to the support in a reliable and economical manner. The clip can be embodied in such a way that the cassette can be removed from the injector again only by destroying the clip.

In order to rule out operating errors, means are advantageously provided to define the direction of rotation of the cassette body and to cause the cassette body to lock into the injection position after pivoting.

In order to avoid an incorrect direction of rotation, the journal (15) is embodied at the underside of the cassette body (13) eccentrically to the longitudinal axis of the cassette body (41). If the cassette body is pivoted in the incorrect direction of rotation, one end of the cassette body abuts the support.

As a result of the special design feature that the journal is shaped in a polygonal manner, the journal is locked in the spring element in the storage position and in the injection position.

The spring element has advantageously a spring element which is arranged in the journal receptacle and has a receiving opening in which the journal can assume at least two locking positions. The spring element causes the journal, or the cassette body molded onto the journal, to lock on the injector in various rotary positions.

BRIEF DESCRIPTION OF THE DRAWINGS

The invention will be described in greater detail hereinafter with reference to the schematic illustration of the figures, in which.

DETAILED DESCRIPTION OF THE ILLUSTRATED EMBODIMENTS

Figure 1:
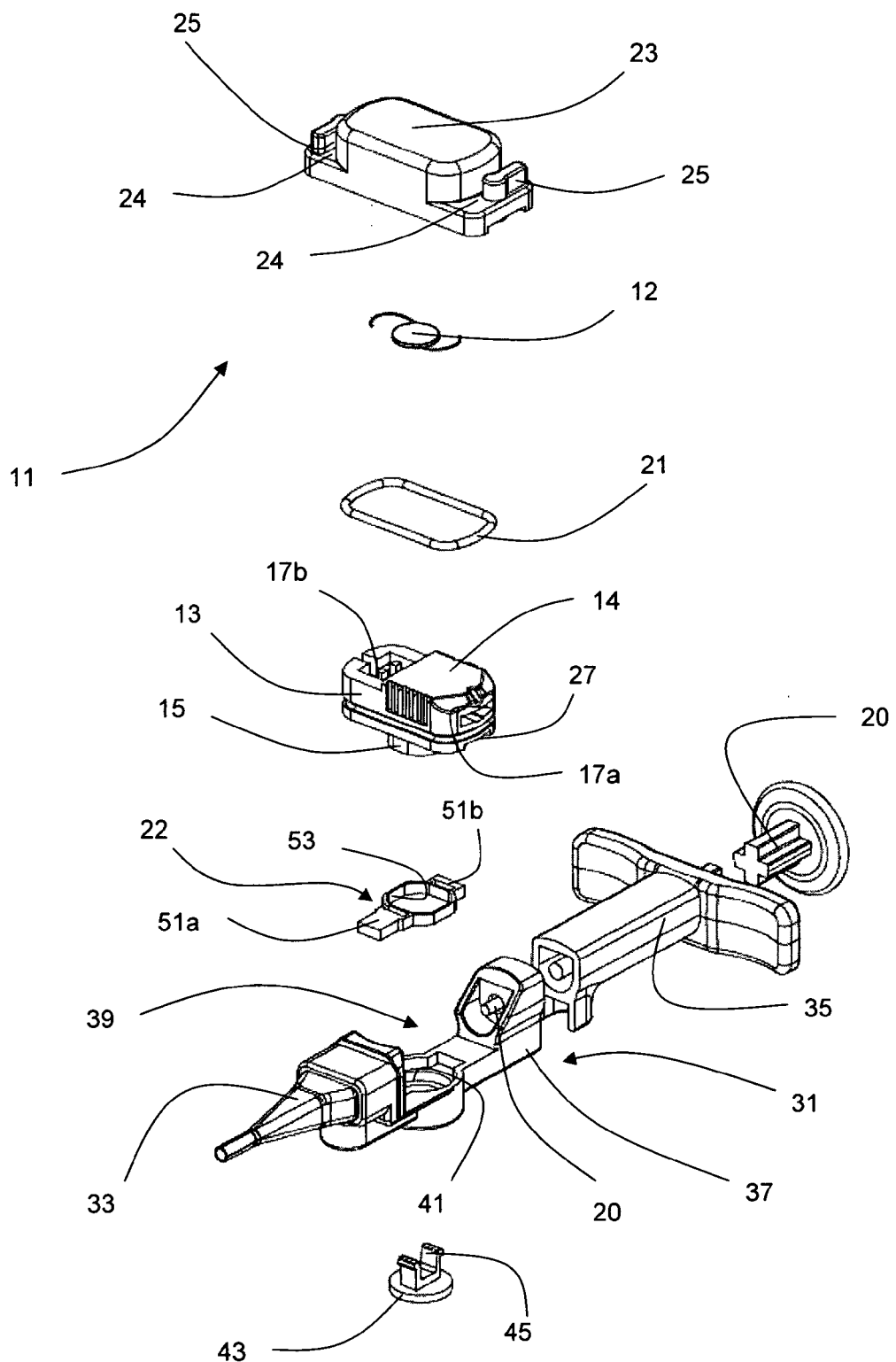
FIG. 1 is an exploded view of an injector system consisting of an injector and cassette consisting of a cassette body and a cassette lid.

FIGS. 1 to 8 show a cassette 11 which serves to store an IOL 12. The cassette 11 is shown in detail in FIGS. 1 and 2. The cassette 11 consists of a cassette body 13, which is partially closed by a cover 14, and a cassette lid 23 for closing the cassette body 13 in a fluid-tight manner. The cassette 11 can be used to inject an IOL 12 into the aperture 39 of an injector 31 (FIGS. 1 and 3 to 8).

The cassette body 13 has a space 19 for receiving an IOL 12. Openings 17a, 17b, through which an injector piston (20) can extend for ejecting an IOL 12, which is received in the receiving space 19, through the opening 17b, are provided on opposing side walls of the cassette body. Means, such as projections, holding-down arrangements and the like, can be provided in the receiving space 19 in order to fix the IOL 12 in a precisely defined position.

Figure 2:
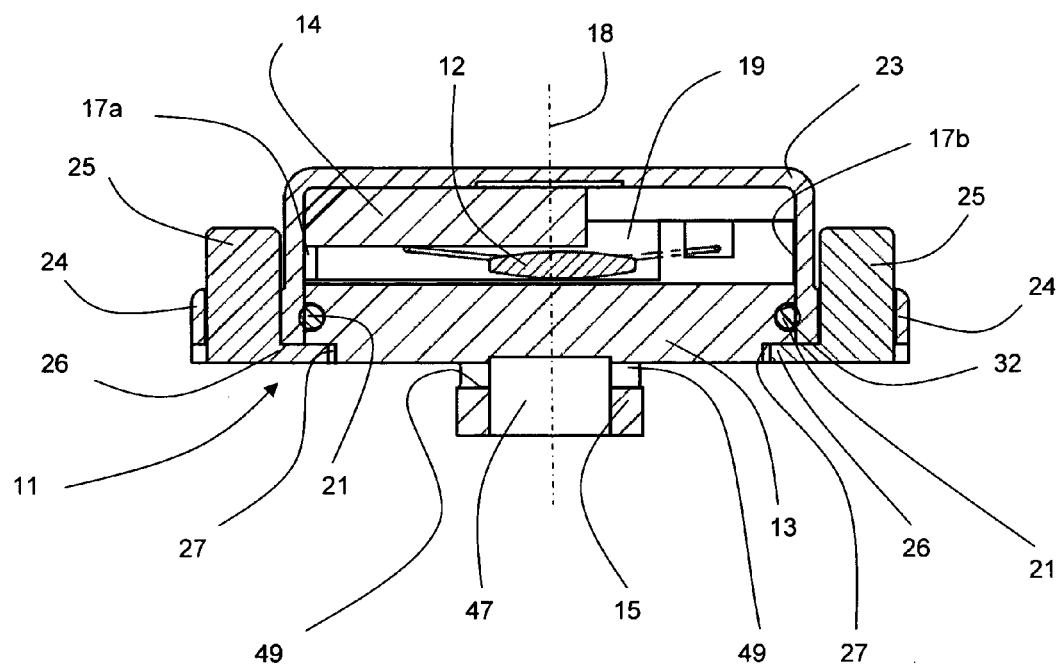
FIG. 2 is a longitudinal section through a cassette body for receiving IOLs.
Figure 3:
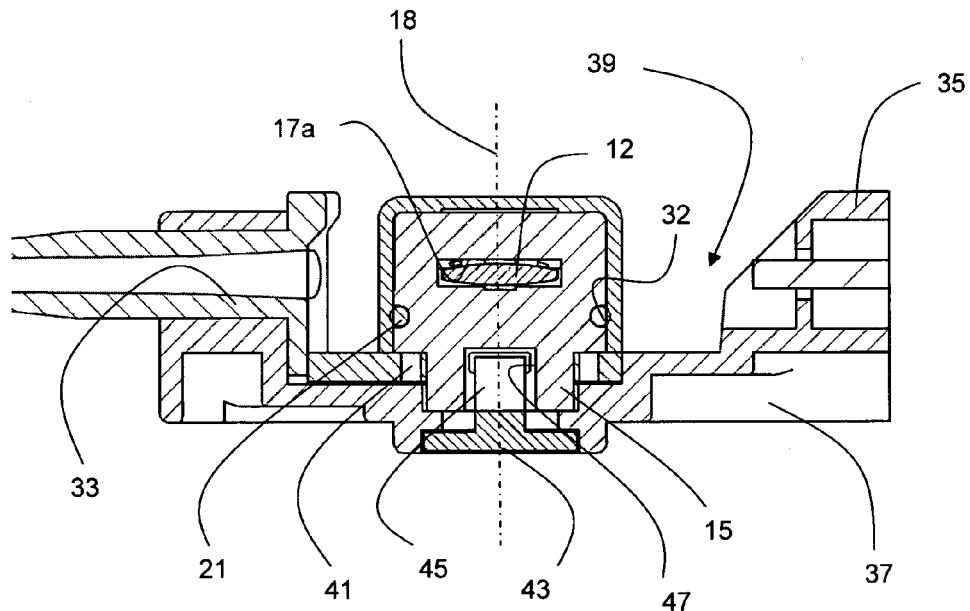
FIG. 3 is a longitudinal section through a detail of an injector with a cassette body in the storage position.
Figure 4:
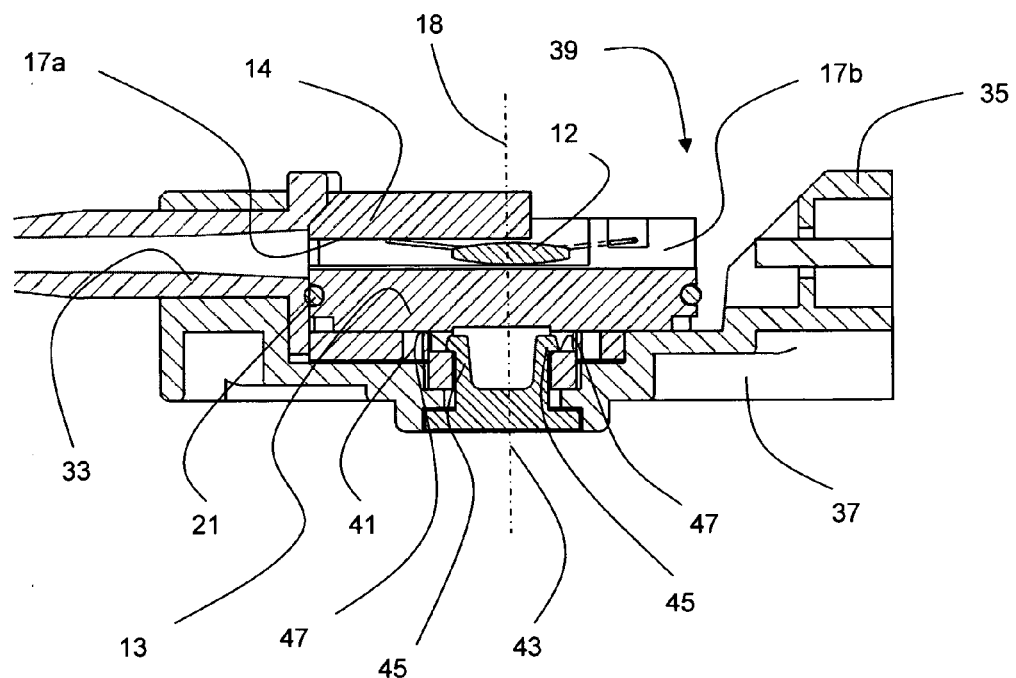
FIG. 4 is a longitudinal section through a detail of an injector with a cassette body in the injection position.

A journal 15, which can be inserted in a journal receptacle 41 of an injector 31 in a form-fitting manner, is molded onto or arranged at the underside of the cassette body 13 (FIGS. 2 to 4 show the cassette 11 and a detail of the injector 31). The journal receptacle 41 is provided centrally at the upper side of the support 37 within the aperture 39. The journal 15 or the cassette body 13 is rotatably fixed in the journal receptacle 41 by a clip 43. The clip has two flexible hooks 45 which extend, in the mounted state, through a cylindrical receptacle 47 of the journal 15, which receptacle has an axis of rotation 18 as its centre line. The flexible hooks 45 are in this case locked into two apertures 49 oriented transversely to the receptacle 47. Once the cassette has been inserted into the injector, then the clip 43 prevents the cassette from being able to be removed again.

Once the cassette has been inserted into the injector 31, then rotation of the cassette body about the axis of rotation 18 extending through the journal 15 is facilitated. In this case, the cassette body can be made to pivot from a storage position, in which the aligned openings 17a, 17b are positioned transversely to the injection direction, into an injection position in which the openings 17a, 17b are aligned with the injection direction. The journal 15 is designed in its cross section as a regular octagon. A spring element 22, which is inserted into the journal receptacle 41, serves to fix the cassette body 13 once the cassette body has been made to pivot into the injection position. The spring element 22 is supported in the journal receptacle 41 by two extensions 51a, 51b so as to be protected from undesirable rotation relative to the injector 31. The spring element 22 consists of, in addition to the extensions 51a, 51b, a regular octagonal resilient ring 53 onto which the extensions 51a, 51b are molded. The octagonal ring 53 surrounds the octagonal journal 15 in a form-fitting manner.

It would also be conceivable for the spring element 22 to be molded onto the injector 31.

When the cassette body 13 is rotated from its storage position into its injection position, the ring 53 releases the journal 15 in a resilient manner until, in the injection position, the sides of the journal come to lie again on the sides of the ring 53 and the journal 15 locks in the ring 53. It is important that the octagonal ring is set apart from the journal receptacle in such a way as to allow rotation of the octagonal ring in the journal receptacle.

In order to ensure that the cassette body 13 is correctly oriented in the injection position, an orientation arrow may be visible on the cover 14. It is also conceivable for the journal 15 to be molded eccentrically onto the underside of the cassette body 14. During rotation in the incorrect direction, the cassette body 14 abuts the injector 31 before the cassette body assumes its injection position. A peripheral ring seal 21, against which the cassette lid 23 rests, in the closed state of the cassette 11, so as to produce a seal, is provided at the outside of the cassette body 13. The ring seal 21 is received in a peripheral groove 32. It is also conceivable for the groove to be provided on the cassette lid, instead of on the cassette body. Two extensions 24 are molded onto the cassette lid 23 at the narrow sides. A pivot lever 25 is arranged centrally and rotatably on each of the extensions. The pivot levers have at their undersides interlocking extensions 26 which, rotated by 90° relative to the pivot levers, are molded onto the pivot levers. During closing of the cassette body 13 by the cassette lid 23, the pivot levers are rotated by 90°. The molded-on interlocking extensions 26 engage with interlocking apertures 27 formed at the bottom at the wide sides of the cassette body 13. The edge of the lid is pressed against the ring seal 21. This reliably prevents undesirable discharge of storage liquid. The cassette 11 is made from a biocompatible plastics material which withstands conventional sterilization temperatures of over 120° C.

FIGS. 5 to 8 show the injector 31 with an injection nozzle 33 and an injector body 35 which are molded onto a support 37. The injector piston 20 extends from the end face remote from the injection nozzle 33 into the injection body 35. The injection nozzle 33 and the injector body 35 are arranged on the support 37 in such a way as to form between the injection nozzle 33 and the injector body 35 the aperture 39 which serves to receive the cassette 11. The length of the aperture 39 corresponds precisely to the distance between the openings 17a and 17b. As a result, in the injection position of the cassette body 13, the transitions between the cassette body 13 and injection nozzle 33 or between the cassette body 13 and injector body The injection system according to the invention functions as follows: during manufacture, the cassette body 13 is fitted with the IOL 12 and storage liquid, hermetically sealed by the cassette lid 23, fixed on the injector 31 in such a way that the mutually aligned openings 17a, 17b are arranged transversely to the injection direction and then sterilized (for example with ETO, gamma rays or in an autoclave). As a result of the fact that the cassette 11 is installed transversely, there is space to fix the cassette 11, together with the cassette lid 23, on the injector 31. Subsequently, the preloaded injection system can be packaged in sterile form in a see-through packaging and delivered to the customer. The dispatch state of the injector system may be seen from FIG. 4. Because the intraocular lens is received in liquid and the receiving space is hermetically dosed off from the environment, the lens may be stored without problem for months and even years. It is however also conceivable for only the cassette to be sterilized and attached to the injector just shortly before implantation.

Figure 5:
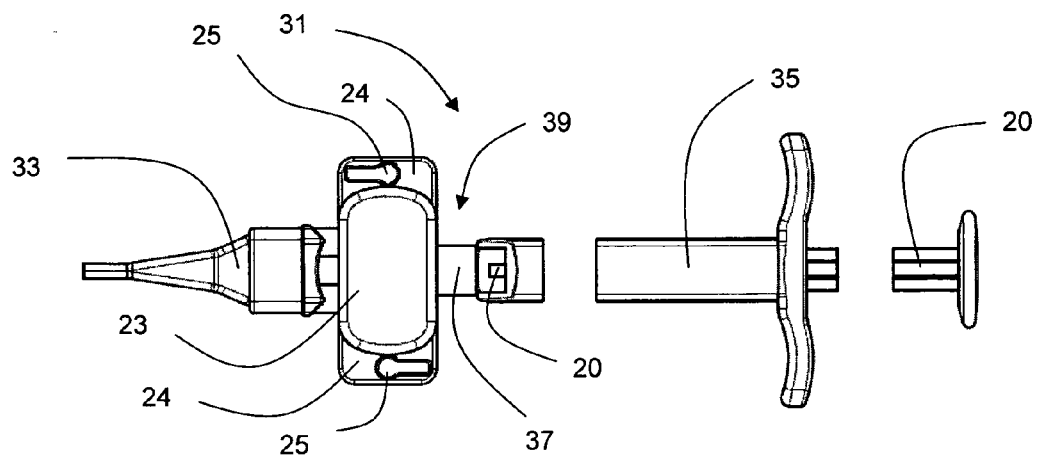
FIG. 5 is a plan view onto an injector system consisting of an injector and an attached, dosed cassette.
Figure 6:
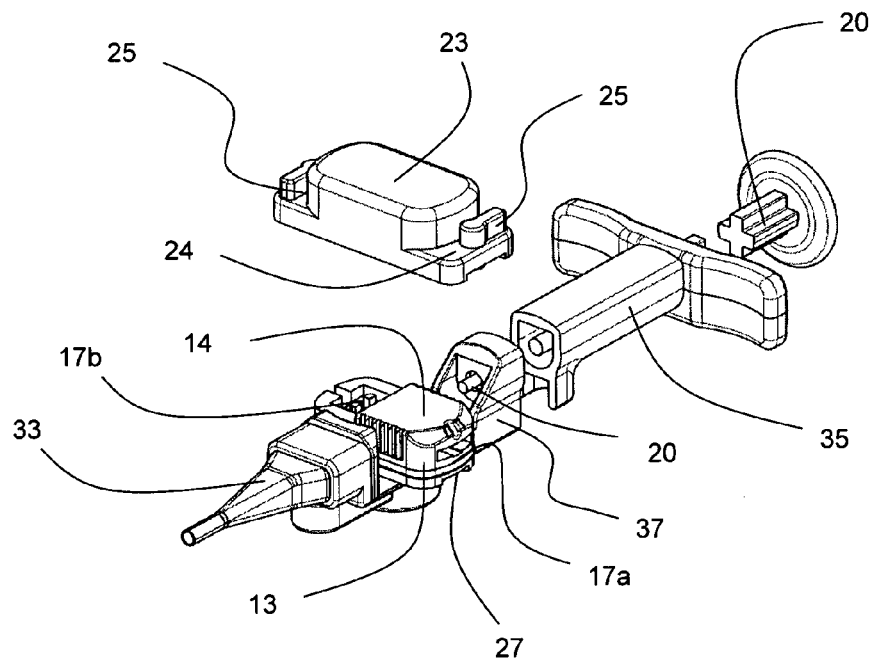
FIG. 6 is a perspective view of the injector system from FIG. 5 with a raised cassette lid.
Figure 7:
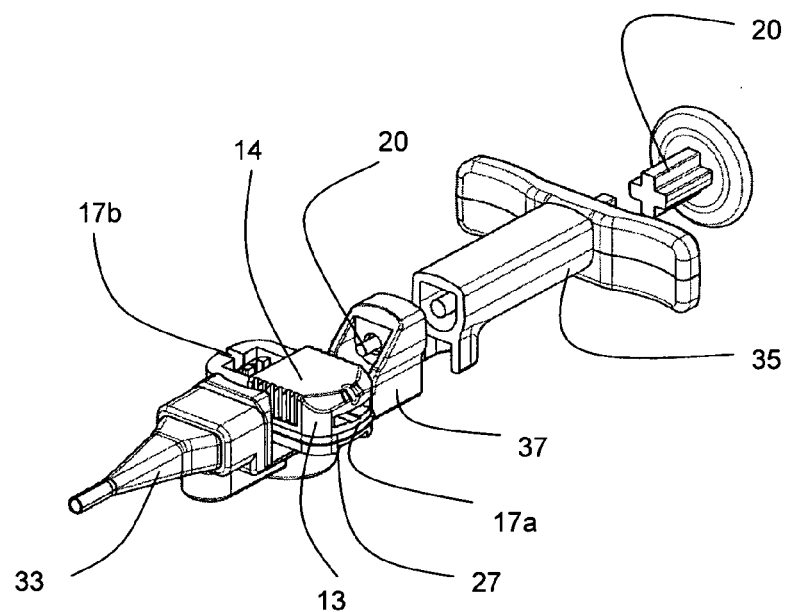
FIG. 7 is a perspective view of the injector system from FIG. 5 with a removed cassette lid.
Figure 8:
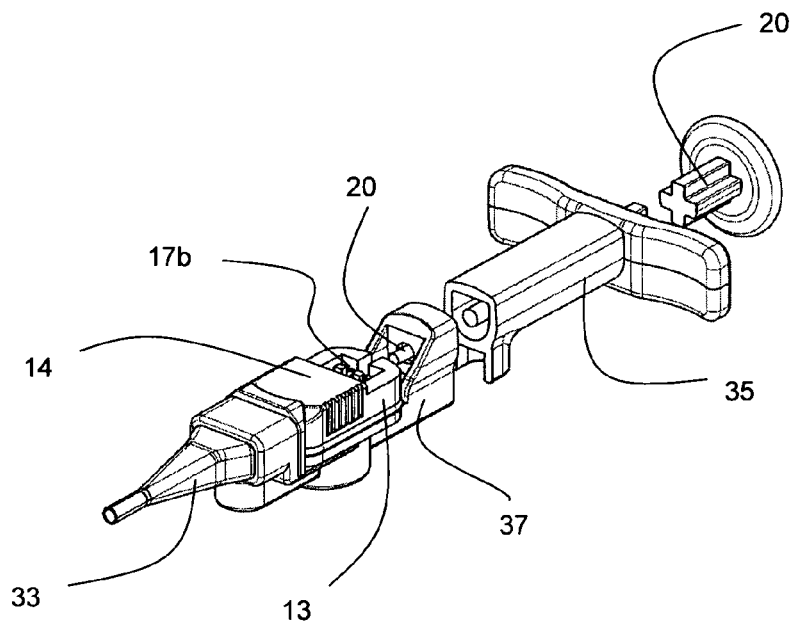
FIG. 8 is a perspective view of the injector system from FIG. 5 with the cassette in the position ready for injection.

For the imminent injection of the IOL, the user removes the preloaded injector system from the packaging, opens the two pivot levers 25 and removes the cassette cover 23. The storage liquid is removed if appropriate (FIG. 5). Afterwards, the IOL receiving space 19 and the injector nozzle are filled with lubricant and the cassette body 13 is rotated by 90° until the guide journal 15 locks in the depression 45. In this position, the cassette is oriented precisely, so that the injector piston can penetrate into the receiving space 19 through the opening 17a and eject the IOL into the injector nozzle through the opening 17b and out of the injector nozzle.

In principle, the liquid-tight cassette according to the invention may be equipped with different coupling means and thus also be used with injectors other than those described above.

The invention claimed is:

1. A cassette comprising:
    a cassette body defining a receiving space for receiving an intraocular lens, the cassette body further defining openings on opposing side walls,
    a cassette lid coupled to the cassette body for closing the receiving space and the openings on opposing side walls of the cassette body thereby hermetically sealing the receiving space of the cassette body, and
    a first coupling structure provided on the cassette body for coupling the cassette body to an injector and to orient the cassette body relative to the injector, when the lid is closed relative to the cassette body.

2. The cassette of claim 1, further comprising a seal disposed between the cassette lid and the cassette body for sealing the cassette lid relative to the cassette body when the lid is closed relative to the cassette body.

3. The cassette of claim 2, wherein the seal is disposed at least partially in a peripheral groove in the cassette body.

4. The cassette of claim 1, wherein the first coupling structure is configured to rotatably engage with a second coupling structure on the injector.

5. The cassette of claim 1, wherein the cassette body has an outside peripheral sealing edge against which the cassette lid can rest in a closed position, so as to produce a seal between the cassette body and the cassette lid.

6. The cassette of claim 1, further comprising interlocking structures on the cassette lid and cassette body to releasably join together the cassette lid and cassette body.

7. The cassette of claim 6, wherein the interlocking structures are formed by two pivot levers disposed at opposing sides of the cassette lid and can be brought into engagement with the cassette body.

8. The cassette of claim 7, further comprising two extensions, on each of which one of the pivot levers is rotatably arranged and each of which is formed onto one of the opposing sides of the cassette lid.

9. The cassette of claim 1, wherein the receiving space is partially closed by the cassette lid.

10. The cassette of claim 1, wherein the cassette lid and cassette body are formed from a biocompatible plastics material.

* * * * *